United States Patent
Driol et al.

(10) Patent No.: US 10,709,409 B2
(45) Date of Patent: Jul. 14, 2020

(54) SYSTEM AND METHOD FOR CONVEYING ONE OR MORE PREDICTIVE INDICATORS OF AN IMAGING CONTROL PARAMETER

(71) Applicant: General Electric Company, Schenectady, NY (US)

(72) Inventors: Clemence Driol, Puteaux (FR); Didier Albert Verot, Voisins le Bretonneux (FR); Lionel Desponds, St-Remy-les-Chevreuse (FR); Julien Miagat, L'Hay-les-Roses (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 267 days.

(21) Appl. No.: 15/461,932

(22) Filed: Mar. 17, 2017

(65) Prior Publication Data
US 2018/0263590 A1 Sep. 20, 2018

(51) Int. Cl.
*A61B 6/02* (2006.01)
*H05G 1/10* (2006.01)
(Continued)

(52) U.S. Cl.
CPC .............. *A61B 6/545* (2013.01); *A61B 6/488* (2013.01); *A61B 6/542* (2013.01); *A61B 6/544* (2013.01); *H04N 5/32* (2013.01)

(58) Field of Classification Search
CPC ......... A61B 6/488; A61B 6/542; A61B 6/544; A61B 6/545; A61B 6/032; A61B 6/405; A61B 6/5205; A61B 6/4233; A61B 6/10; A61B 6/461; A61B 6/463; A61B 6/022; A61B 6/0407; A61B 6/4429; A61B 6/4435; A61B 6/107; A61B 5/055; A61B 6/037; A61B 6/563; A61B 6/566; A61B 8/54; A61B 8/565; A61B 6/4291; A61B 6/4405; A61B 5/23206; A61B 5/23225; G01T 1/02; G06F 19/00; H04N 5/32; H04N 5/23206; H04N 5/23225; H04M 1/03;
(Continued)

(56) References Cited

U.S. PATENT DOCUMENTS

| 2,009,406 | A | 7/1935 | Longley | |
|---|---|---|---|---|
| 6,332,014 | B1 * | 12/2001 | Boutenko | A61B 6/504 348/E5.088 |

(Continued)

OTHER PUBLICATIONS

Extended European Search Report and Opinion issued in connection with corresponding EP Application No. 18160739.1 dated Jul. 4, 2018.

*Primary Examiner* — Irakli Kiknadze
(74) *Attorney, Agent, or Firm* — Grogan, Tuccillo & Vanderleeden, LLP

(57) ABSTRACT

A method for conveying one or more predictive indicators of an imaging control parameter is provided. The method includes: obtaining an initial image acquisition via an imaging system based at least in part on an initial configuration of the imaging system; collecting data regarding the imaging control parameter during the initial image acquisition; and generating the one or more predictive indicators based at least in part on the collected data. Each of the one or more predictive indicators corresponds to a calculated value of the imaging control parameter associated with a potential configuration of the imaging system different from the initial configuration.

19 Claims, 4 Drawing Sheets

(51) Int. Cl.
*A61B 6/00* (2006.01)
*H04N 5/32* (2006.01)

(58) Field of Classification Search
CPC .... H04M 1/0202; H04M 1/0277; H04M 1/62; H04M 1/035; H04M 1/23; H04L 67/02; H04L 63/20; H04L 67/00; H04L 67/26; H04L 67/12; H04L 63/08; H04L 67/10; H04L 67/32; H04L 67/34; H04L 63/105; H04L 63/0823; H04L 63/1441; H04L 67/16; A61K 38/00; G01N 2333/91215; G01N 2500/10; G01N 33/574; G06T 11/006
USPC ............. 378/95–98, 98.5, 8, 42, 207, 62, 68
See application file for complete search history.

(56) References Cited

U.S. PATENT DOCUMENTS

| | | | |
|---|---|---|---|
| 6,768,784 B1 * | 7/2004 | Green | A61B 6/00 378/62 |
| 8,260,025 B2 * | 9/2012 | Walimbe | A61B 6/4441 382/132 |
| 8,503,613 B2 | 8/2013 | Sabol et al. | |
| 2007/0269019 A1 * | 11/2007 | Spahn | G03B 42/02 378/207 |
| 2009/0074143 A1 | 3/2009 | Tsukagoshi et al. | |
| 2009/0262892 A1 | 10/2009 | Haras | |
| 2012/0230470 A1 | 9/2012 | Bertram et al. | |
| 2014/0270053 A1 | 9/2014 | Larson | |
| 2016/0242712 A1 | 8/2016 | Jin et al. | |

* cited by examiner

SYSTEM AND METHOD FOR CONVEYING ONE OR MORE PREDICTIVE INDICATORS OF AN IMAGING CONTROL PARAMETER

BACKGROUND

Technical Field

Embodiments of the invention relate generally to medical imaging systems, and more specifically, to a system and method for conveying one or more predictive indicators of an imaging control parameter.

Discussion of Art

Imaging systems are used by physicians to perform diagnostic analysis and therapeutic procedures by producing images, e.g., exposing a subject/patient to radiation such as x-rays. In many such imaging systems, the production of images is governed by a system configuration that seeks to optimize image quality while staying within certain limits defined by one or more imaging control parameters, e.g., total radiation exposure to a patient during an imaging procedure, signal to noise ratio, etc. For example, in many radiation based imaging systems, larger amounts of radiation typically result in higher image quality. Exposure to certain types of radiation, however, can potentially cause unwanted sides effects in the patient. Thus, the system configurations of many such imaging systems seek to optimize image quality for a given amount of radiation exposure to the patient.

During the course of many imaging procedures, the level of image quality required by the performing physician may vary, e.g., a low image quality may be sufficient for some parts of the procedure while a high image quality may be required for other parts of the procedure. Thus, many imaging systems allow a physician to toggle/select between various system configurations, that correspond to differing levels of image quality, to provide for the adjustment of image quality as needed while minimizing the risk that one or more of the imaging control parameters will be violated/exceeded.

The effects that a particular system configuration will have on an imaging control parameter, however, usually varies during the procedure based on changing environmental factors, e.g., patient thickness. Many algorithms used to estimate/calculate the effect of a system configuration on a given control parameter are complex. Present imaging systems, however, do not calculate/estimate the effect of non-selected system configurations for a given control parameter. Thus, many physicians presently determine if a desired image quality will result in the violation of an imaging control parameter by temporarily switching to the corresponding system configuration and monitoring its effect on the imaging control parameter. Such an approach, however, not only waste time and contrast media, but also unnecessarily increases the risk that one or more control parameters will be exceeded.

What is needed, therefore, is an improved system and method for conveying one or more predictive indicators of an imaging control parameter.

BRIEF DESCRIPTION

In an embodiment, a method for conveying one or more predictive indicators of an imaging control parameter is provided. The method includes: obtaining an initial image acquisition via an imaging system based at least in part on an initial configuration of the imaging system; collecting data regarding the imaging control parameter during the initial image acquisition; and generating the one or more predictive indicators based at least in part on the collected data. Each of the one or more predictive indicators corresponds to a calculated value of the imaging control parameter associated with a potential configuration of the imaging system different from the initial configuration.

In another embodiment, an imaging system for conveying one or more predictive indicators of an imaging control parameter is provided. The imaging system includes an imaging device configured to generate one or more images, and a controller in electronic communication with the imaging device. The controller is operative to: obtain an initial image acquisition via the imaging device based at least in part on an initial configuration of the imaging system; collect data regarding the imaging control parameter during the initial image acquisition; and generate the one or more predictive indicators based at least in part on the collected data. Each of the one or more predictive indicators corresponds to a calculated value of the imaging control parameter associated with a potential configuration of the imaging system different from the initial configuration.

In yet another embodiment, a non-transitory computer readable medium storing instructions is provided. The stored instructions are configured to adapt a controller of an imaging system to: obtain an initial image acquisition via an imaging device of the imaging system based at least in part on an initial configuration of the imaging system; collect data regarding an imaging control parameter of the imaging system during the initial image acquisition; and generate the one or more predictive indicators of the imaging control parameter based at least in part on the collected data. Each of the one or more predictive indicators depicts a calculated value of the imaging control parameter corresponding to a potential configuration of the imaging system different from the initial configuration.

DRAWINGS

The present invention will be better understood from reading the following description of non-limiting embodiments, with reference to the attached drawings, wherein below:

DETAILED DESCRIPTION

Figure 1:
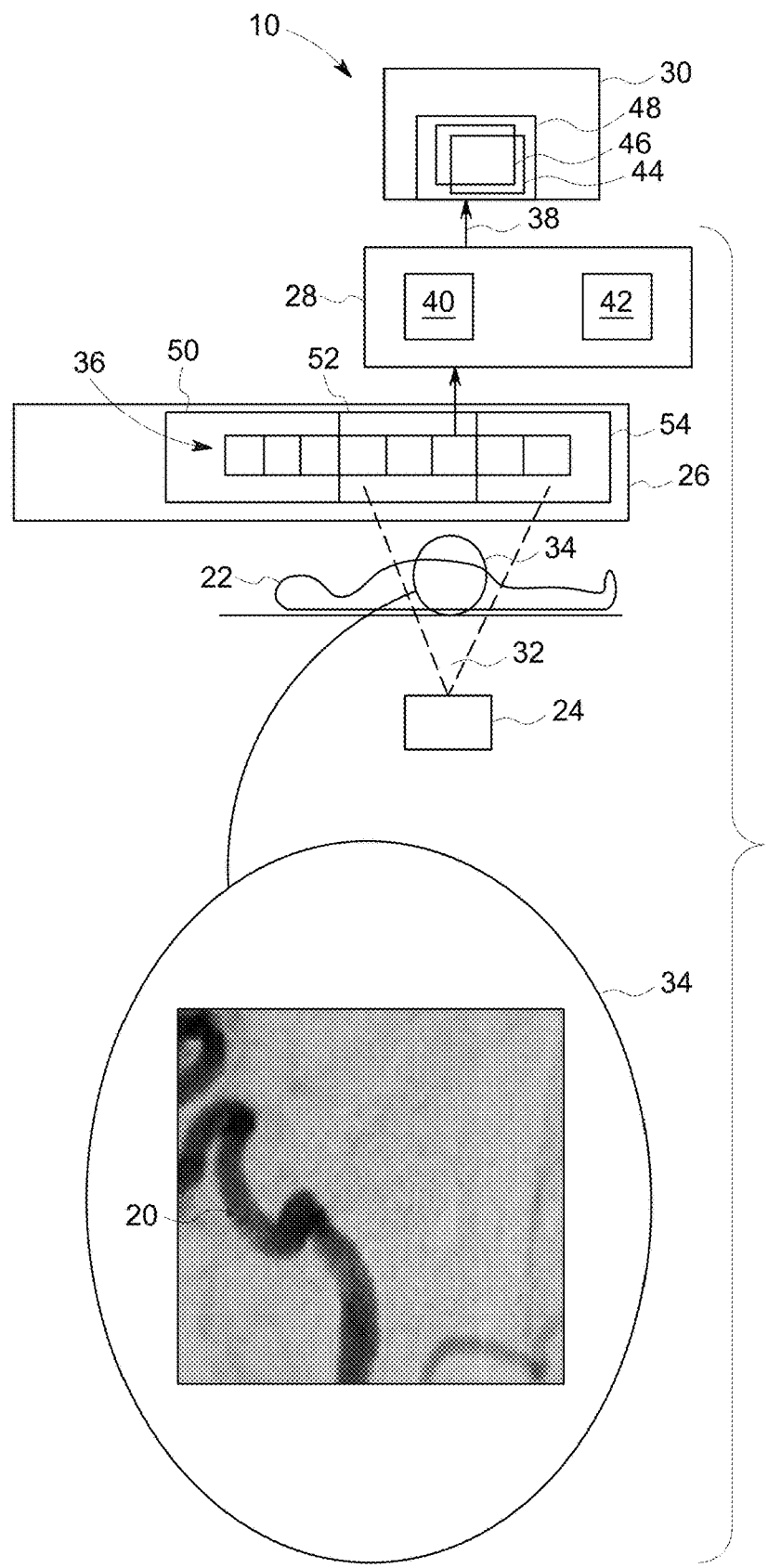
FIG. 1 is a block diagram of an exemplary imaging system for conveying one or more predictive indicators of an imaging control parameter in accordance with an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. As further used herein, the terms "imaging procedure" and/or "medical imaging procedure" refer to a medical procedure that involves an imaging system to assist in accomplishing one or more tasks. Accordingly, as also used herein, the term "task" means an objective of a medical procedure, e.g., deploying/installing a stent into a blood vessel, locating an ulcer, imaging a clogged artery, suturing a patient, and/or other medical processes. Further, the term "imaging control parameter," as used herein, refers to a factor/property that effects and/or governs the acquisition of one or more images via an imaging system, e.g., the maximum amount of radiation allowed for use to generate the one or more images. The terms "configuration," "system configuration," and "configuration of the system," as used herein with respect to imaging systems, refer to a state and/or mode of operation of the imaging system corresponding to one or more desired imaging control parameters, e.g., an imaging system may have a first state for acquiring images via high amounts of radiation to obtain a desired high image quality, and a second state, different from the first state, for acquiring images having low image quality while using a desired low amount of radiation. For example, an Interventional Image Guided System ("IGS") may have the following three configurations: 1) Receptor Dose Limited Plus ("RDL+") Low 7.5 fps; 2) IQ Standard ("IQst") Low 15 fps; and 3) IQ Plus ("IQ+") Normal 15 fps. As used herein, the term "radiation dose" refers to the rate of radiation exposure, e.g., mGy/min. Similarly, the term "total radiation exposure," as used herein with respect to an imaging procedure, refers to the total amount of radiation that a patient is exposed to during the imaging procedure. As also used herein, the terms "display," "displaying," "displays," "depict," "depicts," and "depicting" mean communicating through light, e.g., a computer display, and/or sound, e.g., speakers.

Additionally, while the embodiments disclosed herein are described with respect to an x-ray based imaging system, e.g., a fluoroscopic imaging system, it is to be understood that embodiments of the present invention are equally applicable to other devices such as Magnetic Resonance Imaging ("MRI") systems, real-time endoscopic imaging, and/or any other type of imaging system having various system configurations that effect imaging control parameters. As will be appreciated, embodiments of the present invention related imaging systems may be used to analyze objects within any material which can be internally imaged, generally. As such, embodiments of the present invention are not limited to analyzing objects within human tissue.

Referring now to FIG. 1, an imaging system 10 for conveying one or more predictive indicators 12 and 14 (FIG. 2) of an imaging control parameter 18 (FIG. 2) is shown. As will be understood, the imaging system 10 is operative to image at least one object 20, e.g., an internal organ, blood vessel, etc., within a subject/patient 22. For example, the imaged subject 22 may be a patient undergoing an angioplasty procedure, and the imaged object 20 may be a blood vessel into which a stent is to be deployed. As shown in FIG. 1, the system 10 includes: a radiation source 24 and a detector 26, which collectively form an imaging device; a controller 28; and a display screen 30. The radiation source 24 projects a radiation beam 32 through an area of interest 34 of the imaged subject 22 within which the object 20 is disposed. The radiation beam 32 is received by the detector 26, which generates a plurality of images 36 that are then communicated to the controller 28, which generates a video feed 38 that is transmitted to and displayed by the display screen 30.

As further shown in FIG. 1, the controller 28 includes at least one processor/CPU 40 and at least one memory device 42, and is in electronic communication with the radiation source 24, detector 26, and/or the display screen 30. An imaging program/application may be stored in the at least one memory device 42 that, when loaded into the at least one processor 40, adapts the controller 28 to generate the video feed 38 by processing the images 36 received from the detector 26. In embodiments, the imaging program may further adapt the controller 28 to control the detector 26 and/or the radiation source 24.

The video feed 38 includes a plurality of frames 44, 46, and 48. As used herein, the term frame describes a composite image that may be based at least in part on one or more of the plurality of images 36 acquired by the imaging system 10. For instance, in embodiments, a single composite image/frame 44 may be generated by registering one or more of the acquired images 36 to a reference image selected from the plurality of images 36. The registration of one or more images 36 to a reference image may increase the contrast of the object 20 within the produced/generated frame 44. Accordingly, in embodiments, each frame 44, 46, and 48 may be based at least in part on one or more of the images 36 received by the controller 28 from the detector 26. Once a frame 44 has been generated, it is transmitted, as part of the video feed 38, by the controller 28 to the display screen 30. In other words, in embodiments, the displayed video feed 38 is a processed form of the raw images 36 acquired by the system 10. In embodiments, the video feed 38 may be a live/real-time and/or near-real-time feed. In other embodiments, one or more of the frames 44, 46, and 48 may be still images, e.g., a photograph.

As will be understood, the imaging system 10 may acquire one or more images 36 as part of an image acquisition 50, 52, 54, wherein the images 36 within the same acquisition 50, 52, 54, are acquired via the same system configuration. As such, the controller 30 may be operative to obtain an initial image acquisition 50 (depicted as a collection of three images 36) via the imaging device, i.e., the radiation source 24 and detector 26, based at least in part on an initial configuration of the imaging system 10. As such, the controller 28 collects data regarding the imaging control parameter 18 during the first image acquisition 50, and then generates the one or more predictive indicators 12 and 14 based at least in part on the collected data. The controller 28 may then display the one or more predictive indicators 12 and 14, e.g., on the display screen 30 and/or through speakers. As will be appreciated, each of the one or more predictive indicators 12 and 14 is associated with and/or depicts a calculated value of the imaging control parameter 18 corresponding to a potential configuration of the imaging system 10 different from the initial configuration.

Figure 2:
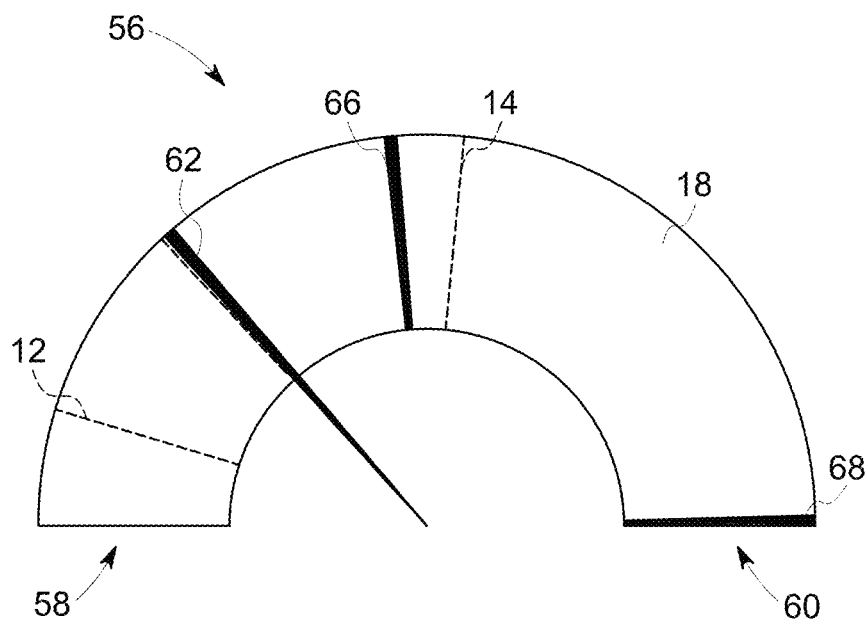
FIG. 2 is a diagram of the one or more predictive indicators conveyed by the system of FIG. 1 in accordance with an embodiment of the invention.
Figure 3:
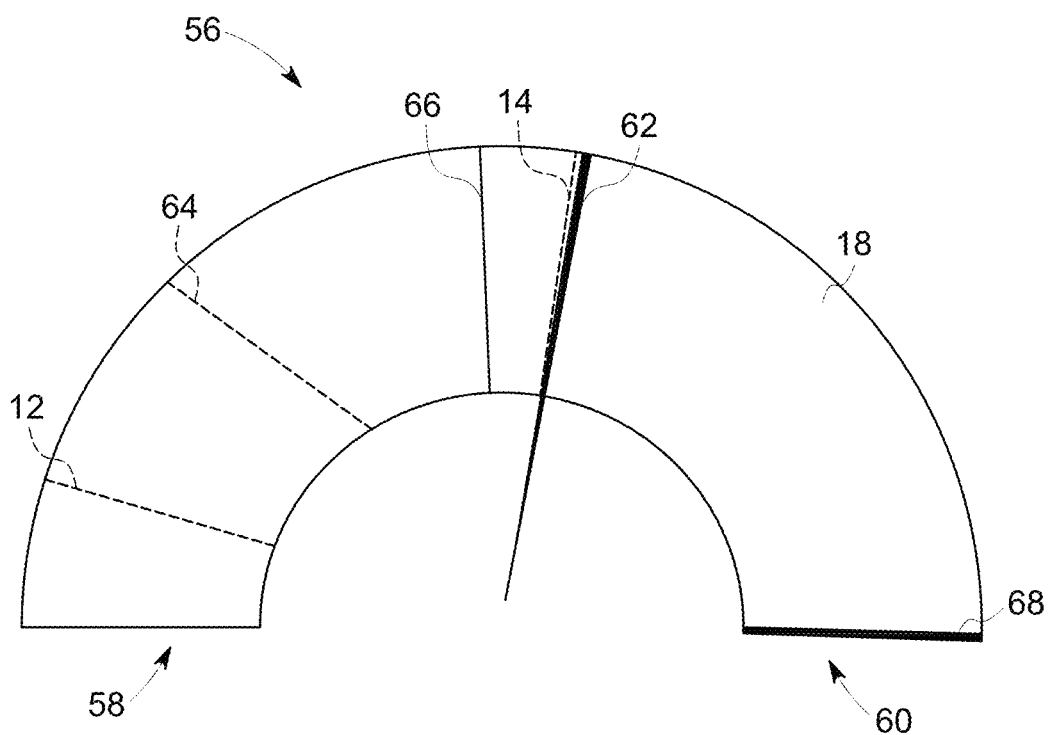
FIG. 3 is another diagram of the one or more predictive indicators conveyed by the system of FIG. 1 in accordance with an embodiment of the invention.
Figure 4:
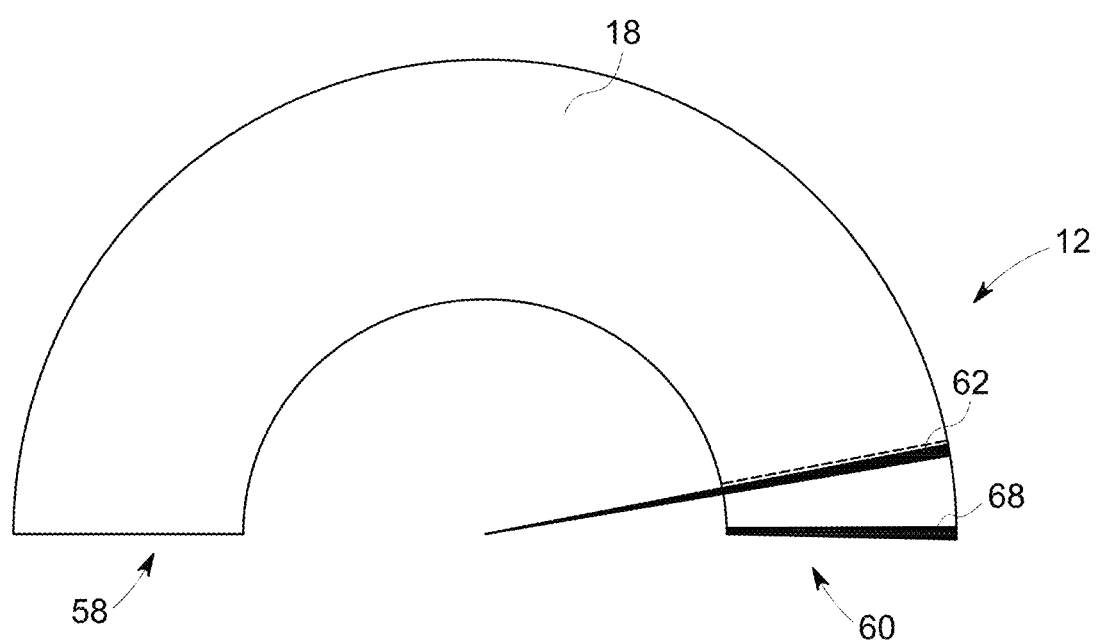
FIG. 4 is another diagram of the one or more predictive indicators conveyed by the system of FIG. 1 in accordance with an embodiment of the invention.
Figure 5:
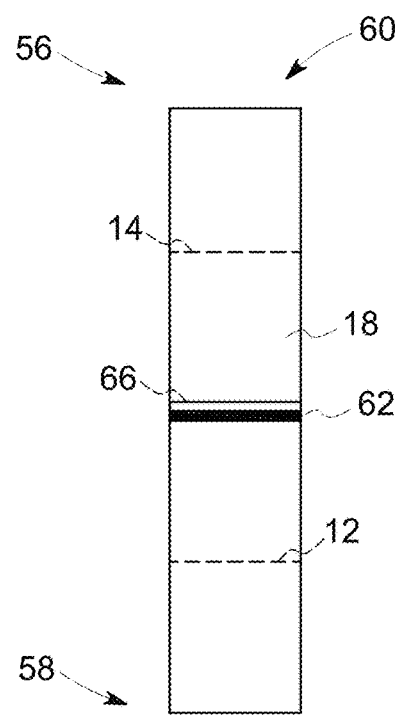
FIG. 5 is another diagram of the one or more predictive indicators conveyed by the system of FIG. 1 in accordance with an embodiment of the invention.
Figure 6:
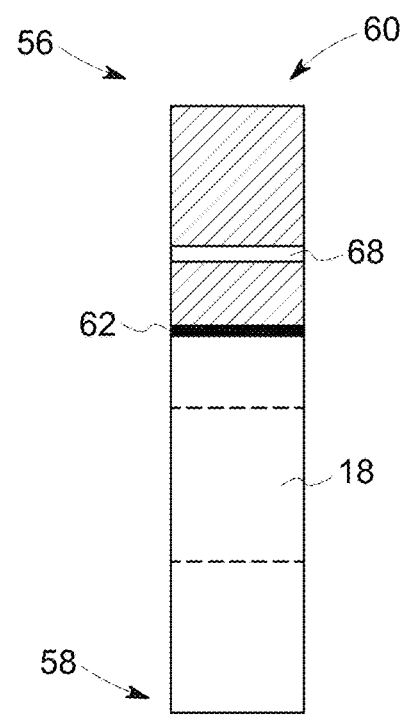
FIG. 6 is another diagram of the one or more predictive indicators conveyed by the system of FIG. 1 in accordance with an embodiment of the invention.

As illustrated in FIG. 2, the controller 28 may generate a graphical display 56 that depicts various values of the imaging control parameter 18 as an arc (as shown in FIGS. 2-4) and/or as a vertical column (as shown in FIGS. 5 and 6) having a first end 58 and a second end 60 that represent minimum and maximum values for the imaging control parameter 18, respectively. The controller 28 may further depict a current indicator 62 that corresponds to the value of the imaging control parameter 18 resulting from the current configuration of the system 10. The controller 28 may then generate the first predictive indicator 12 and/or the second predictive indicator 14 which respectively correspond to the calculated/predicted values of the imaging control parameter 18 for system configurations having a lower and higher image quality than the current system configuration.

For example, as stated above, the imaging system 10 may be a fluoroscopic imaging system utilized by a physician to perform a medical task, e.g., deployment of a stent within an artery 20 of a patient 22. As will be appreciated, the physician may desire to limit the total radiation exposure of the patient 22 during the imaging procedure, i.e., radiation dose is an imaging control parameter 18 of the imaging system 10. Accordingly, the physician may set the initial configuration of the imaging system 10 to a configuration corresponding to a medium image quality level that results in a medium radiation dose to the patient 22.

The controller 28 then obtains an initial/first image acquisition 50 at the desired medium image quality, while, as stated above, the controller 28 also collects data regarding the radiation dose 18 to the patient 22 via one or more sensors. As such, in certain aspects, the collected data may include a measurement of the radiation dose 18 received by the patient 22, a measurement of the thickness of the patient 22, and/or other factors relevant to determining and/or predicting/calculating the radiation dose 18 received by the patient 22. The controller 28 then generates the one or more predictive indicators 12 and 14 via applying the collected data to an internal model that predicts the amount of radiation dose 18 to the patient 22 for both a potential system configuration corresponding to an image quality lower than the initial system configuration, as well as a potential system configuration corresponding to an image quality higher than the initial system configuration. Thus, as will be appreciated, the controller 28 executes one or more configuration scenarios prior to the next image acquisition, i.e., in parallel. The generated predictive indicators 12 and 14 are then displayed by the controller 28, e.g., on the display screen 30, along with the current indicator 62, such that the first 12 and second 14 predictive indicators show the calculated radiation dose 18 to the patient 22 should the physician select either the lower or higher image quality configuration, respectively. Thus, the physician is able to simultaneously view the radiation dose 18 being received by the patient 22 at the current configuration/image quality, and the radiation doses 18 the patient 22 will most likely receive if the system 10 is moved to the lower or higher image quality configuration.

Accordingly, suppose the physician begins the imaging procedure at the medium image quality configuration as stated above. After the initial imaging acquisition 50, the current indicator 62 may show that the medium image quality configuration is resulting in a radiation dose of 23.4 mGy/min to the patient 22, and the predictive indicators 12 and 14 may show that the low and high image quality configurations might result in radiation doses of 10.1 mGy/min and 50.1 mGy/min, respectively.

The physician, after having determined that a higher image quality is needed to perform the current task, and that the predicted 50.1 mGy/min radiation dose is acceptable, may select/transition the imaging system 10 to the higher image quality configuration. Accordingly, as illustrated in FIG. 3, the controller 28 obtains a second/subsequent image acquisition 52 (depicted as a collection of three images 36 in FIG. 1) at the desired high image quality resulting in an increased radiation dose to the patient 22. As before during the initial image acquisition 50, the controller 28 again collects data regarding the radiation dose 18 received by the patient 22 during the subsequent image acquisition 52, and then generates and/or updates the one or more predictive indicators 12 and 14 based at least in part on the collected data. The controller 28 then displays the new and/or updated predictive indicators 12 and 14, e.g., on the display screen 30. For example, as shown in FIG. 3, the current indicator 62, predicative indicator 12, and a newly generated predicative indicator 64 corresponding to the previously selected medium image quality configuration, may show that the radiation dose to the patient 22 under the selected/current high image quality configuration is resulting in the previously predicted 50.1 mGy/min, and that the low and medium image quality configurations might result in 10.1 mGy/min and 23.4 mGy/min, respectively.

After completing the task for which the high image quality was desired, the physician, seeking to conserve the total amount of radiation dose 18 to the patient 22 for the whole imaging procedure, may then select/transition the imaging system 10 to the low image quality configuration after having determined that a lower image quality would be acceptable for the next task. Accordingly, the controller 28 will proceed to acquire an additional/third image acquisition 54 (depicted as a collection of two images 36 in FIG. 1) at the desired low image quality, which in turn results in a lower radiation dose 18 to the patient 22. As before during the prior two image acquisitions 50 and 52, the controller 28 again collects data on the radiation dose 18 received by the patient 22 during the additional image acquisition 54, which is in turn used to update the one or more shown predicative parameters 12 and 64, and/or to generate new/additional predictive parameters.

Returning back to FIG. 2, as will be appreciated, in embodiments, the controller 24 may further display one or more limit indicators 66 and 68 that depict limits of the imaging control parameter 18 that should and/or cannot be exceeded by the imaging system 10. For example, continuing with the above fluoroscopy example, the limit indicator 66 may correspond to a user defined limit, e.g. a target radiation dose limit entered by the physician, while the limit indicator 68 may correspond to an industry regulation, e.g., a maximum radiation dose limit mandated by a governing medical agency, such as the maximum air kerma rate (21 CFR 1020.32) for preset startup, and/or a design limitation of the imaging system 10, e.g., the maximum radiation dose that the detector 26 is capable of receiving prior to becoming damaged. For example, the physician may set a self-imposed radiation limit of 41.6 mGy/min (represented by limit indicator 66), and, as depicted in FIG. 2, the predictive indicator 14 may show that the physician will likely exceed the self-imposed limit 66 should the high image quality configuration be selected. Similarly, FIG. 4 depicts a situation where the physician may simply be unable to obtain a higher image quality as there are no predictive indicators shown between the current indicator 62 and the limit indicator 68, which may correspond to a limitation of the system 10, i.e., the imaging system 10 is "maxed out."

As will be appreciated, while the above example was discussed in terms of fluoroscopy with the imaging control parameter 18 being the radiation dose to the patient 22, it will be understood that in embodiments, the imaging control parameter 18 may be another factor such as power usage of the imaging system 10, and/or an image quality metric, e.g., a signal to noise ratio, a contrast to noise ratio, noise, a d' index, and/or an image brightness. Additionally, the system configurations may correspond to factors other than desired image quality, e.g., high, medium, and/or low power usage.

As will be further appreciated, the controller 28 may continuously collect/sample the data regarding the imaging control parameter 18 and update the predictive indicators 12 and 14 in real-time. In such embodiments, the predictive indicators 12 and 14 may move within the graphical display 56 as one or more imaging control parameters change during the imaging procedure while the imaging system 10 remains in the same configuration. For example, suppose that the physician again begins a fluoroscopic imaging procedure with the imaging system 10 in the medium image quality configuration as shown in FIG. 2. Further suppose after the initial image acquisition 50, that the predictive indicator 14 shows the radiation dose 18 corresponding to the high image quality configuration exceeds the self-imposed limit 66. As the amount of radiation dose corresponding to a system configuration for a desired image quality level typically depends on the thickness of the patient 22 at the actual site of imaging, e.g., the thinner the part of the patient 22 being imaged the less radiation required to obtain a particular image quality, the physician can attempt to bring the high image quality system configuration back within the self-imposed limit 66 by adjusting the thickness of the patient 22 at the site of imaging.

Accordingly, the controller 28 updates the predictive indicator 14 based on collected data that reflects the changes in the patient 22 thickness. In other words, the physician can view the effect of the adjustments to the patient 22 thickness on the predicted radiation dose corresponding to the high image quality system configuration in real-time, and can continue to adjust the thickness until the predictive indicator 14 shows that the predicted radiation dose 18 for the high image quality system configuration is below the self-imposed limit 66. As will be understood, the aforementioned example of the real-time generation and display of the predictive parameter 14 is equally applicable to other imaging control parameters, limits, and types of imaging systems. As such, the data collected by the controller 28 regarding the imaging control parameter 18 may include: other image quality metrics, e.g., detector dose, patient dose, x-ray generation techniques specific criteria; detector matrix panel size, x-ray generation focal spot size, etc.; and/or power factors, e.g., ray tube power.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a method for conveying one or more predictive indicators of an imaging control parameter is provided. The method includes: obtaining an initial image acquisition via an imaging system based at least in part on an initial configuration of the imaging system; collecting data regarding the imaging control parameter during the initial image acquisition; and generating the one or more predictive indicators based at least in part on the collected data. Each of the one or more predictive indicators corresponds to a calculated value of the imaging control parameter associated with a potential configuration of the imaging system different from the initial configuration. In certain embodiments, the imaging control parameter is a radiation dose, a power usage of the system, or an image quality metric. In certain embodiments, the image quality metric is at least one of a signal to noise ratio, a contrast to noise ratio, noise, a d' index, and an image brightness. In certain embodiments, the potential configuration is based at least in part on a desired image quality. In certain embodiments, the data regarding the imaging control parameter is at least one of a measured value of the imaging control parameter, a thickness of a subject imaged by the imaging system, a detector dose, a patient dose, and an x-ray generation factor. In certain embodiments, the method further includes selecting the potential configuration; and obtaining a subsequent image acquisition via the imaging system based at least in part on the selected potential configuration. In certain embodiments, the method further includes displaying the one or more predictive indicators. In certain embodiments, the method further includes displaying a limit indicator of the imaging control parameter. In certain embodiments, the limit indicator is defined by at least one of a user of the imaging system, an industry regulation, and a design limitation of the imaging system.

Other embodiments provide for an imaging system for conveying one or more predictive indicators of an imaging control parameter. The imaging system includes an imaging device configured to generate one or more images, and a controller in electronic communication with the imaging device. The controller is operative to: obtain an initial image acquisition via the imaging device based at least in part on an initial configuration of the imaging system; collect data regarding the imaging control parameter during the initial image acquisition; and generate the one or more predictive indicators based at least in part on the collected data. Each of the one or more predictive indicators corresponds to a calculated value of the imaging control parameter associated with a potential configuration of the imaging system different from the initial configuration. In certain embodiments, the imaging control parameter is a radiation dose, a power usage of the system, or an image quality metric. In certain embodiments, the image quality metric is at least one of a signal to noise ratio, a contrast to noise ratio, noise, a d' index, and an image brightness. In certain embodiments, the potential configuration is based at least in part on a desired image quality. In certain embodiments, the data regarding the imaging control parameter is at least one of a measured value of the imaging control parameter, a thickness of a subject imaged by the imaging device, a detector dose, a patient dose, and an x-ray generation factor. In certain embodiments, the controller is further operative to provide for the selection of the potential configuration; and obtain a subsequent image acquisition via the imaging device based at least in part on the selected potential configuration. In certain embodiments, the controller is further operative to display the one or more predictive indicators. In certain embodiments, the controller is further operative to display a limit indicator of the imaging control parameter.

Yet still other embodiments provide for a non-transitory computer readable medium storing instructions. The stored instructions are configured to adapt a controller of an imaging system to: obtain an initial image acquisition via an imaging device of the imaging system based at least in part on an initial configuration of the imaging system; collect data regarding an imaging control parameter of the imaging system during the initial image acquisition; and generate the one or more predictive indicators of the imaging control parameter based at least in part on the collected data. Each of the one or more predictive indicators depicts a calculated value of the imaging control parameter corresponding to a potential configuration of the imaging system different from the initial configuration. In certain embodiments, the imaging control parameter is a radiation dose, a power usage of the system, or an image quality metric. In certain embodiments, the image quality metric is at least one of a signal to noise ratio, a contrast to noise ratio, noise, a d' index, and an image brightness.

Accordingly, as will be appreciated, by calculating and displaying predictive indicators of imaging control parameters for an imaging system, some embodiments of the invention allow physicians performing a medical imaging procedure to see the predicted radiation dose of a configuration of the imaging system without having to first transition the imaging system to the configuration. Thus, some embodiments of the present invention reduce and/or eliminate the amount of trial and error in determining whether a particular desired image quality can be achieved without exceeding certain limits, e.g., maximum allowable radiation dose. As such, some embodiments of the invention reduce the overall radiation dose of a patient for certain medical imaging procedures.

Further, by automating the calculation of the predicted value, e.g., radiation dose, for a given system configuration based on data sampled in real-time during the imaging procedure, some embodiments of the invention reduce the work load on, and/or improve the confidence of, the physician performing the imaging procedure.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A method for conveying one or more predictive indicators of an imaging control parameter comprising:
   obtaining an initial image acquisition via an imaging system based at least in part on an initial configuration of the imaging system, the initial image acquisition including one or more projective images;
   collecting data regarding the imaging control parameter during the initial image acquisition;
   generating the one or more predictive indicators based at least in part on the collected data;
   displaying a limit indicator of the imaging control parameter, the limit indicator based at least in part on the one or more predictive indicators;
   adjusting the configuration of the imaging system; and
   updating the one or more predictive indicators based at least in part on additional data collected during a subsequent image acquisition via the imaging system in the adjusted configuration, wherein when the imaging system is in the initial configuration, each of the one or more predictive indicators corresponds to a calculated value of the imaging control parameter associated with a potential configuration of the imaging system different from the initial configuration.

2. The method of claim 1, wherein the imaging control parameter is a radiation dose, a power usage of the system, or an image quality metric.

3. The method of claim 2, wherein the image quality metric is at least one of a signal to noise ratio, a contrast to noise ratio, noise, a d' index, and an image brightness.

4. The method of claim 1, wherein the potential configuration is based at least in part on a desired image quality.

5. The method of claim 1, wherein the data regarding the imaging control parameter is at least one of a measured value of the imaging control parameter, a thickness of a subject imaged by the imaging system, a detector dose, a patient dose, and an x-ray generation factor.

6. The method of claim 1 further comprising:
   selecting the potential configuration; and
   obtaining a subsequent image acquisition via the imaging system based at least in part on the selected potential configuration.

7. The method of claim 1 further comprising:
   displaying the one or more predictive indicators.

8. The method of claim 1, wherein the limit indicator is defined by at least one of a user of the imaging system, an industry regulation, and a design limitation of the imaging system.

9. An imaging system for conveying one or more predictive indicators of an imaging control parameter comprising:
   an imaging device configured to generate one or more images;
   a controller in electronic communication with the imaging device and operative to:
      obtain an initial image acquisition via the imaging device based at least in part on an initial configuration of the imaging system, the initial image acquisition including one or more projective images;
      collect data regarding the imaging control parameter during the initial image acquisition;
      generate the one or more predictive indicators based at least in part on the collected data;
      display a limit indicator of the imaging control parameter, the limit indicator based at least in part on the one or more predictive indicators; and
      update the one or more predictive indicators based at least in part on additional data collected during a subsequent image acquisition via the imaging system in an adjusted configuration,
      wherein when the imaging system is in the initial configuration, each of the one or more predictive indicators corresponds to a calculated value of the imaging control parameter associated with a potential configuration of the imaging system different from the initial configuration.

10. The system of claim 9, wherein the imaging control parameter is a radiation dose, a power usage of the system, or an image quality metric.

11. The system of claim 10, wherein the image quality metric is at least one of a signal to noise ratio, a contrast to noise ratio, noise, a d' index, and an image brightness.

12. The system of claim 9, wherein the potential configuration is based at least in part on a desired image quality.

13. The system of claim 9, wherein the data regarding the imaging control parameter is at least one of a measured value of the imaging control parameter, a thickness of a subject imaged by the imaging device, a detector dose, a patient dose, and an x-ray generation factor.

14. The system of claim 9, wherein the controller is further operative to:
   provide for the selection of the potential configuration; and
   obtain a subsequent image acquisition via the imaging device based at least in part on the selected potential configuration.

15. The system of claim 9, wherein the controller is further operative to:
   display the one or more predictive indicators.

16. A non-transitory computer readable medium storing instructions configured to adapt a controller of an imaging system to:
   obtain an initial image acquisition via an imaging device of the imaging system based at least in part on an initial configuration of the imaging system, the initial image acquisition including one or more projective images;
   collect data regarding an imaging control parameter of the imaging system during the initial image acquisition;
   generate the one or more predictive indicators of the imaging control parameter based at least in part on the collected data;
   display a limit indicator of the imaging control parameter, the limit indicator based at least in part on the one or more predictive indicators;
   update the one or more predictive indicators based at least in part on additional data collected during a subsequent image acquisition via the imaging system in an adjusted configuration,
   wherein when the imaging system is in the initial configuration, each of the one or more predictive indicators depicts a calculated value of the imaging control parameter corresponding to a potential configuration of the imaging system different from the initial configuration.

17. The non-transitory computer readable medium of claim 16, wherein the imaging control parameter is a radiation dose, a power usage of the system, or an image quality metric.

18. The non-transitory computer readable medium of claim 17, wherein the image quality metric is at least one of a signal to noise ratio, a contrast to noise ratio, noise, a d' index, and an image brightness.

19. An imaging system for conveying one or more predictive indicators of an imaging control parameter comprising:
- an imaging device configured to generate one or more images;
- a controller in electronic communication with the imaging device and operative to:
  - obtain an initial image acquisition via the imaging device based at least in part on an initial configuration of the imaging system, the initial image acquisition including one or more projective images;
  - collect data regarding the imaging control parameter during the initial image acquisition;
  - generate the one or more predictive indicators based at least in part on the collected data; and
  - update the one or more predictive indicators based at least in part on additional data collected during a subsequent image acquisition via the imaging system in an adjusted configuration;
- wherein:
- each of the one or more predictive indicators corresponds to a calculated value of the imaging control parameter associated with a potential configuration of the imaging system different from the initial configuration; and
- the imaging control parameter is at least one of a power usage of the system, a signal to noise ratio, a d' index, and an image brightness.

* * * * *